United States Patent [19]

Wallace

[11] 4,154,342

[45] May 15, 1979

[54] STERILIZABLE PACKAGE

[75] Inventor: Henry G. Wallace, Frinton-on-Sea, England

[73] Assignee: Boehringer Ingelheim GmbH, Ingelheim am Rhein, Fed. Rep. of Germany

[21] Appl. No.: 819,950

[22] Filed: Jul. 28, 1977

[30] Foreign Application Priority Data

Jul. 30, 1976 [GB] United Kingdom ............... 31791/76

[51] Int. Cl.² ...................... B65D 83/00; B65D 33/18; A61B 19/02
[52] U.S. Cl. .................................... 206/439; 128/221; 229/62.5
[58] Field of Search ................... 128/214 C, 221, 272; 150/9; 206/204, 363, 439, 484.1, 524.1, 528; 229/62.5

[56] References Cited

U.S. PATENT DOCUMENTS

| | | | |
|---|---|---|---|
| 3,032,182 | 5/1962 | Bechtold | 206/439 |
| 3,092,249 | 6/1963 | Chapman | 206/439 X |
| 3,157,481 | 11/1964 | Bujan | 128/221 X |
| 3,229,813 | 1/1966 | Crowe, Jr. et al. | 206/439 |
| 3,435,948 | 4/1969 | Kaganov et al. | 206/439 |
| 3,468,471 | 9/1969 | Linder | 206/439 X |
| 4,022,324 | 5/1977 | Schuster | 206/439 |

*Primary Examiner*—Davis T. Moorhead
*Attorney, Agent, or Firm*—Hammond & Littell

[57] ABSTRACT

A sterilizable package for medical or surgical instruments or the like, said package consisting essentially of a rigid or semi-rigid container including a filter element made of porous plastic and adapted to allow the passage of a sterilizing gas therethrough, but prevent the entry of bacteria into the package.

6 Claims, 1 Drawing Figure

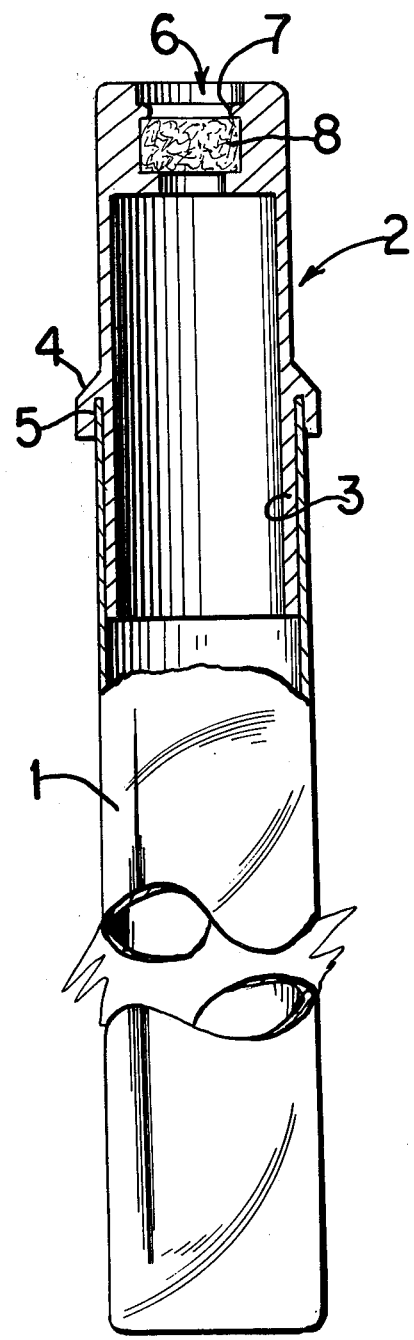

STERILIZABLE PACKAGE

This invention relates to a sterilizable package for medical or surgical instruments or the like.

BACKGROUND OF THE INVENTION

Medical and surgical instruments are commonly packed in a package which allows the passage of gases for sterilization purposes. For example, they may be sealed in a paper package which is then placed in an atmosphere of ethylene oxide under pressure. The gas passes through the paper into the package to sterilize the contents thereof, and then the package is left in the air, generally at atmospheric pressure, to vent the sterilizing gas. Because of the toxic nature of ethylene oxide when introduced into the human body it is necessary that the venting process should be substantially completed before the contents of the package are used. This requirement necessitates the relatively free passage of gas through the walls of the package.

A serious disadvantage of such paper packages is that they are susceptible to damage; such damage may be caused by contact with a sharp object or by rough handling, or the contents of the package may rupture the walls, particularly when the packed instrument includes a needle. Of course, when a sterilized package is damaged, the ingress of bacteria becomes a possibility, and the sterility of the contents of the package can no longer be assumed.

In an attempt to alleviate the problem of damage, rigid or semi-rigid packages have been proposed. A typical example is a tubular package made of cellulose acetate. Such packages have the advantage that they allow observation of the contents of the package. However, owing to the low rate of diffusion of sterilizing gas through the walls of such packages, it is necessary to provide a filter element in a wall to allow the passage of gas, while preventing the entry of bacteria. The use of filter elements has again led to problems in preventing damage and maintaining sterility. An example of a prior proposal is a tubular package provided at one end with a surgical cotton plug. Such plugs are particularly susceptible to damage and, furthermore, if they are moistened they become ineffective in preventing the ingress of bacteria. Other prior proposals include the use of a disc of a thin, porous plastic film or other thin filter material, heat-sealed onto the end of a tubular package. The strength of such filters is inadequate and, furthermore, heat-sealing around a circular line has proved unreliable and contamination of the contents of the package has occurred. There is, moreover, no simple way of checking the integrity of such a seal.

THE INVENTION

According to the present invention, there is provided a sterilizable package comprising a rigid or semi-rigid container including a filter element made of a porous plastic material, the filter element being adapted to allow the passage of gas therethrough, while preventing the passage of bacteria therethrough and being at least as thick as the thinnest part of the rest of the package.

The filter element is preferably a plug of porous polyethylene 1 to 5 mm, preferably about 3 mm, thick retained in an end cap of the package by a retaining ring integral with the end cap. This method of retaining the filter element is easy to carry out in manufacture and provides an effective seal around the edges of the filter element.

An embodiment of the invention will now be described by way of example and with reference to the accompanying drawing in which the sole FIGURE is a partial longitudinal cross-section of a package according to the present invention suitable for sterile packaging of a cannula, catheter or other surgical device.

The package comprises a rigid or semi-rigid transparent container 1 and an end cap 2. The container 1 may consist of a tube of cellulose acetate closed at its lower end and open at its upper end, and the end cap 2 may be made of polyethylene, for example. The cap 2 includes a tubular portion 3 sized to fit closely within the open end of the container 1, and the portion 3 is provided with a raised flange 4 defining a recess 5. The recess 5 is adapted to receive the open end of the container 1 and affords it protection from damage and contamination.

The end cap 2 has an orifice 6 at one end to provide for the inlet and outlet of gas and air. Molded integrally with the end cap 2 is a retaining member in the form of a retaining ring 7 for retaining in position a porous plastic filter element 8.

The filter element 8 may be made of a thermosetting plastic material, such as polyurethane foam, but is preferably made of a thermoplastic material, such as porous polyethylene or polyvinyl chloride. Such materials have the advantage that they are hydrophobic and do not readily allow the passage of bacteria, even when exposed to moisture.

The filter element 8 is to some extent resilient, which enables it to be pushed into position under the retaining ring 7 such that a good seal is formed around the edge of the filter element. This feature avoids the need for heat-sealing, which, as mentioned above, can be unreliable. The element 8 is at least as thick as the thinnest part of the rest of the package and is preferably from 1 to 5 mm thick. A particularly preferred form of filter element 8 consists of a plug of porous polyethylene about 3 mm thick. Filter elements of this thickness are convenient to handle and may be easily fitted into the cap 2.

The size of the pores of the filter element 8 should be such that the filter forms an effective barrier against the entry of bacteria into the package. It is not necessary that the pores should be smaller than bacteria (such as 0.2 microns as in the prior art), provided the filter element is sufficiently thick. In this case, the pores effectively define a labyrinthine path into the package through which gases can pass, while bacteria are unable to pass through the filter.

An important advantage arising from the use of a porous plastic filter element is that the filter can be as resistant to damage as the rest of the package and does not represent a weak point in the package.

The filter element 8 may be retained in the cap 2 by heat-sealing or by a separately formed retaining member. However, simple insertion in the manner described above is believed to be simpler and more reliable.

In use, a medical or surgical instrument is placed into the container 1, and the cap 2 is placed over the open end of the container such that the recess 5 receives the open end of container 1. A sealing band, for example a so-called shrink ring, such as a band of film imprinted with the word "sterile", is positioned around the joint between the container 1 and cap 2 and over the flange 4. The shrink ring, shrinks to seal the joint and thereafter serves to show that the package has not been opened. The package and its contents are then placed into a vacuum and subsequently ethylene oxide or other sterilizing gas, which penetrates the filter element 8 and sterilizes the contents of the package. The sterilizing gas is drawn out and the package is then left in an atmosphere of air to elute. The contents of the package will then remain sterile until the package is opened, the filter element 8 serving to prevent the entry of bacteria.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A container for medical or surgical instruments to be gas-sterilized, said container consisting of a substantially gas-impermeable, open-ended plastic receptable adapted to receive a medical or surgical instrument, a substantially gas-impermeable plastic closure cap tightly covering the open end of said receptacle and having an aperture therein, and a porous plastic filter element mounted within said closure cap to entirely cover said aperture, said filter element being adapted to allow the passage of gases into and out of said container while preventing the passage of bacteria into said container, and the thickness of said filter element being at least as great as the thinnest part of the container.

2. A container of claim 1, where the filter element is from 1 to 5 mm thick.

3. A container of claim 1, where the filter element is about 3 mm thick.

4. A container of claim 1, where the filter element is made of porous polyethylene.

5. A container of claim 1, where said closure cap comprises a retaining member arranged to retain the filter element in position.

6. A container of claim 1, where the closure cap includes a tubular extension provided with an external flange defining a recess to receive a tubular open end of the receptacle.

* * * * *